US006066161A

United States Patent [19]

Parella

[11] Patent Number: 6,066,161

[45] Date of Patent: May 23, 2000

[54] BABY PACIFIER APPARATUS WITH REMOTE CONTROL LOCATOR

[76] Inventor: Nicole D. X. Parella, 10 Travis St., Apt. #3, Worcester, Mass. 01604

[21] Appl. No.: 08/910,578

[22] Filed: Jul. 26, 1997

[51] Int. Cl.[7] .............................. A61M 5/00; A63H 5/00; A63H 30/00; A63H 33/26

[52] U.S. Cl. ............................ 606/234; 446/81; 446/175; 446/485

[58] Field of Search ............................. 446/81, 175, 485, 446/484, 219; 606/234, 235, 236

[56] References Cited

U.S. PATENT DOCUMENTS

| | | | |
|---|---|---|---|
| 5,033,864 | 7/1991 | Lasecki et al. | 606/234 X |
| 5,059,215 | 10/1991 | Girau | 606/234 |
| 5,109,864 | 5/1992 | Lu | 606/234 X |
| 5,292,335 | 3/1994 | Shin | 606/234 |
| 5,522,847 | 6/1996 | Kalis et al. | 606/234 |
| 5,598,143 | 1/1997 | Wentz | 340/539 |
| 5,662,685 | 9/1997 | Uhler | 606/234 |
| 5,859,585 | 1/1999 | Fleming | 606/234 X |

*Primary Examiner*—D Neal Muir

[57] ABSTRACT

A baby pacifier apparatus designed and integrated with a locator device that will illuminate and or sound with a musical tone when activated by a remote transmitter device in order to aid caretakers in locating the pacifier if it is misplaced. The baby pacifier comprises a nipple securely attached to a pacifier flange. The pacifier flange is removably attached to a plastic case. The plastic case houses the locator device which includes a locator device receiver, musical or chime module, light emitting diode and power source. The plastic case is detachably secured to the exterior face of the pacifier flange to allow for sterilization and replacement of worn parts. The locator device receiver is designed to respond to a signal sent from a remote transmitter device. When activated by the remote transmitter device, the locator device receiver will respond by selectively activating the light emitting diode thereby illuminating the unit and or activating the musical or chime module making a sound. In addition, the musical or chime module can be activated by the remote transmitter device for an extended playing period for the child's amusement or comfort.

8 Claims, 2 Drawing Sheets

BABY PACIFIER APPARATUS WITH REMOTE CONTROL LOCATOR

BACKGROUND OF THE INVENTION

1. Field of the Invention

The invention relates to a baby pacifier, and more specifically to a pacifier that incorporates a locator device activated by a remote transmitter to find the pacifier when misplaced by the baby. The locator device includes a receiver circuit that selectively includes sound and or illumination elements.

2. Description of Prior Art

In general pacifiers have been traditionally comprised of a nipple, a mouth guard, and a handle. The designs for pacifiers have been developed to meet the needs of various infants using such variations as orthopedically designed nipples, pleasing designs to look at, temperature sensing devices and soothing sounds as baby suckles on the pacifier. However, few designs have successfully incorporated the needs of the caretaker as well as those of the infant.

One such design has attempted to meet some of the caretakers and needs and that is an illuminated pacifier, U.S. Pat. No. 4,716,902 to Swartz (1988). This pacifier was specifically designed to locate the pacifier if lost in the crib bedding at night. It seemed to do a better job than some other illuminating pacifiers, such as U.S. Pat. No. 5,522,848 to Kanali (1996) of U.S. Pat. No. 5,007,924 to Jekel (1989) which were simply made of luminescent material. One pacifier came closer, U.S. Pat. No. 5,540,719 which comprises a night light system with detachable glow in the dark pacifiers. Never-the-less, the pacifiers were still difficult to find because the luminescent quality will inevitably wear off usually by the time you start to look for it.

The present invention surpasses these limitations and broadens the usefulness of a locator device in the pacifier. It incorporates the use of sound as well as light to simplify and speed up the often frustrating process of pacifier searching.

SUMMARY OF THE INVENTION

The apparatus disclosed in detail below is of a form that is both practical and economical to manufacture to promote wide use. The apparatus comprises a nipple shaped first piece that is securely attached to a flange being the second piece. In its preferred embodiment the nipple is made of soft plastic material that is transparent and the flange is made of hardened plastic material. In addition to its preferred form the nipple and flange may be made of other materials that are approved for use in baby pacifiers. The flange may be made of flexible rubber to avoid potential injury. The flange is removably attached to a case being the third piece. The case houses the locator device. The locator device includes a locator device receiver, a musical module, a light emitting diode and a power source. The case is removably attached to the surface of the flange that is opposite the surface attached to the nipple thereby permitting removal of the nipple and flange as a unit for sterilization and also removal of the case for replacement of worn or inoperative parts. This removal feature of the case also allows for replacement of the entire case in the event the locator device becomes inoperative. A remote transmitter device is used to activate the locator device receiver. The transmitter and receiver are tuned to a plurality of fixed frequencies. The frequencies selected are within the ranges that do not require a special licensing. The frequencies selected are such as to operate even when a clear line of site is not available between the remote transmitter device and the locator device receiver. The remote transmitter device includes a selector, the selector determines which of the plurality of frequencies will be used. The frequency related permits the operator to activate the musical module only, the light emitting diode only or both simultaneously. The musical module may be activated for prolonged use to provide the baby with soothing sounds. The apparatus is therefore not limited to use solely at home but rather may be used while on a drive or a trip as the entire system is easily transportable. The musical module may include several options such as chimes, children songs or nursery rhymes. The transmitter and receiver could be designed to operate on one frequency with codes.

The invention uses a transmitter and receiver to carry out its functions, allowing the caretaker to find the missing pacifier using light in a dark situation or sound when the object cannot be found by sight alone. The caretaker also has the advantage of entertaining and soothing the baby by choosing to have the pacifier musical modular device to play for an extended period of time.

Overall, it is the present inventions objective to aid the caretaker in locating the desired pacifier quickly and efficiently, whether it is misplaced amongst the bedding or lost in an avalanche of toys no matter whether the room is dark or in full daylight.

It is also my desired objective to soothe and amuse the baby with a quality pacifier that uses pleasing designs and musical tones and also takes into consideration the physical differences between children and chose design and shape that will accommodate all nose and facial shapes.

Another objective is to provide the caretaker with a device that is childsafe, but also allows the pacifier to be sterilized or worn parts replaced by being designed in such a way that the case holding electronic components, LED and musical module can be detachably secured to the nipple and flange.

While the invention will he described in connection with a preferred embodiment, it will be understood that I do not intend to limit the invention to that embodiment. On the contrary, I intend to cover all alterations, modifications and equivalents as may be included with the spirit and scope of the invention as defined by the appended claims.

BRIEF DESCRIPTION OF THE DRAWINGS

The object and features of the invention may be understood with reference to the following detailed description of a illustration embodiment of the invention, taken together with the accompanying drawings in which.

DESCRIPTION OF THE PREFERRED EMBODIMENT

Figure 1:
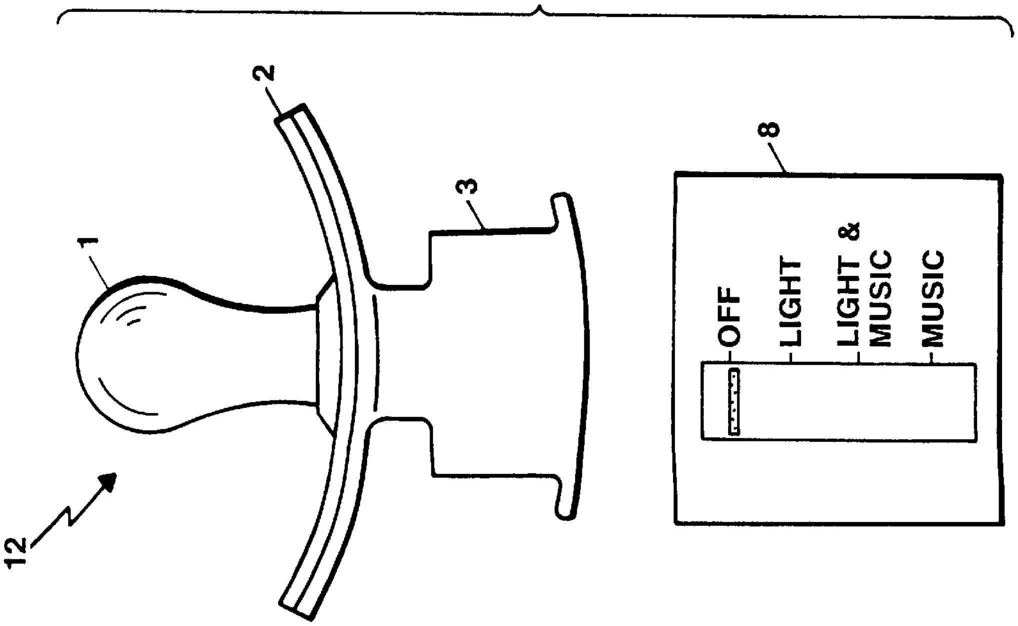
FIG. 1 there is shown the Baby Pacifier Apparatus with Remote Control Locator (12). The nipple (1), flange (2) and case (3) are shown as a unit. The remote transmitter device (8) is shown as a separate unit.

Turning first to FIG. 1 there is shown the Baby Pacifier Apparatus with Remote Control Locator (12). The nipple (1), flange (2) and case (3) are shown as a unit. The remote transmitter device (8) is shown as a separate unit.

Figure 2:
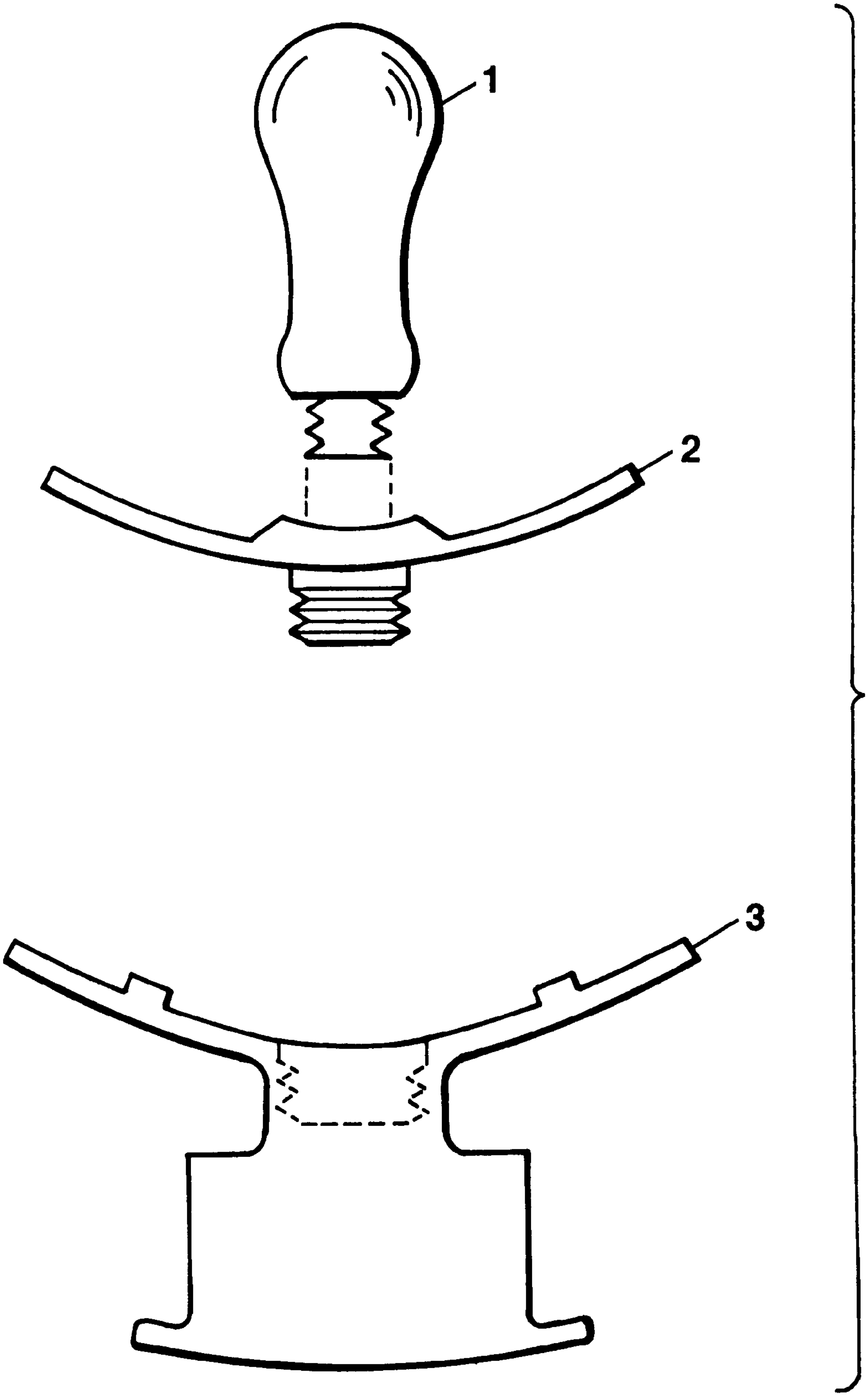
FIG. 2 illustrates the nipple (1), flange (2) and case (3) as separate parts.

FIG. 2 illustrates the nipple (1), flange (2) and case (3) as separate parts.

Figure 3:
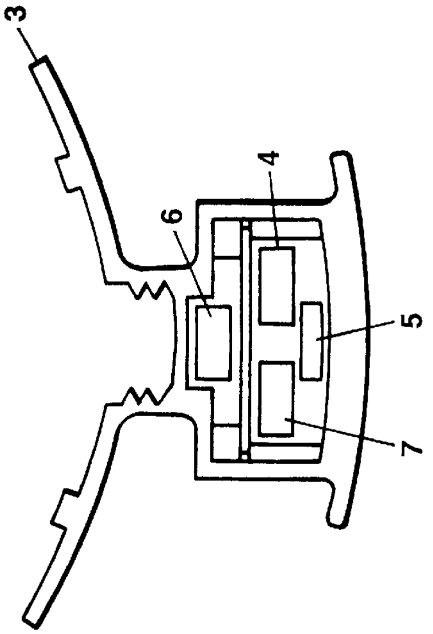
FIG. 3 illustrates an exploded view of the case (3) with the locator device receiver (4), musical module (5), light emitting diode (6) and receiver power source (7) being shown.

FIG. 3 illustrates an exploded view of the case (3) with the locator device receiver (4), musical module (5), light emitting diode (6) and receiver power source (7) being shown.

Figure 4:
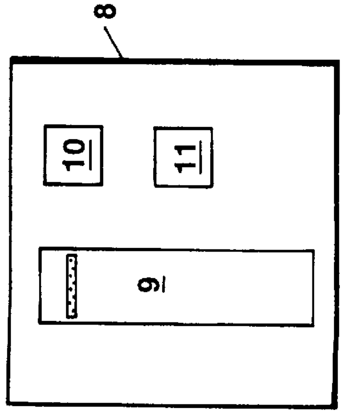
FIG. 4 illustrates an exploded view of the remote transmitter device (8) indicating the selector (9) that would be used to activate the musical module (5) alone, the light emitting diode (6) alone or both simultaneously, transmitter (10) and transmitter power source (11).

FIG. 4 illustrates an exploded view of the remote transmitter device (8) indicating the selector (9) that would be used to activate the musical module (5) alone, the light emitting diode (6) alone or both simultaneously, transmitter (10) and transmitter power source (11).

The circuit used for the locator device includes the locator device receiver (4), musical module (5), light emitting diode (6) and receiver power source (7) are all standard items readily available in the market place. The circuit used for the remote transmitter device includes switch (9), transmitter (10) and transmitter power source (11) are all standard items readily available in the market place.

From the foregoing description it will be apparent that modifications can be made to the apparatus without departing from the teaching of the present invention. Accordingly, it is distinctly understood that the invention is not limited to the preferred embodiment but may be embodied and practiced within the scope of the following claims.

What is claimed is:

1. A remotely locatable pacifier comprising:

(a) a nipple having an opened end and a closed end;

(b) a flange having a top surface and a bottom surface, wherein said nipple open end is coupled to said flange top surface;

(c) a locator case coupled to said flange bottom surface, wherein said locator case houses a receiver locator circuit including:

(i) a receiver configured to receive a locator signal and generate at least one enabling signal responsive to said locator signal;

(ii) a music module operatively coupled to said receiver and configured to generate preselected audible tones responsive to said at least one enabling signal;

(iii) a light emitting diode (LED) operatively coupled to said receiver and configured to illuminate responsive to another of said at least one enabling signal; and (iv) a power source;

wherein said the receiver locator circuit is configured to selectively operate in one of a plurality of operational modes and generate said audible tones and illuminate said LED either in concert or independently in response to said locator signal; and, (d) a remote transmitter case housing a transmitter circuit comprising:

(i) a user controllable selector having a plurality of mode settings, wherein each mode setting corresponds at least one of said operational modes;

(ii) a remote transmitter under operative control of said selector and configured to generate and transmit at a preselected frequency said locator signal, wherein said locator signal corresponds to said mode setting; and (iii) a power source.

2. A remotely locatable pacifier according to claim 1 wherein said nipple shaped first piece is made of a translucent material.

3. A remotely locatable pacifier according to claim 1 wherein said flange is rigidly coupled to said nipple.

4. A remotely locatable pacifier according to claim 1 wherein said flange is removably coupled to said nipple.

5. A remotely locatable pacifier as in claim 1 wherein said LED is located within said case and at least a portion of said case is sufficiently transparent such that said portion of said case is illuminated when the LED is illuminated.

6. A remotely locatable pacifier as in claim 1 wherein said operational modes include:

(A) a first mode wherein said only audible tones are generated;

(B) a second mode wherein only said LED illuminates; and (C) a third mode wherein said audible tones are generated and said LED is illuminated in concert.

7. A remotely locatable pacifier as in claim 1 wherein said LED illuminates in a preselected flashing pattern.

8. A remotely locatable pacifier comprising:

(a) a nipple having an open end and a closed end and comprised of a translucent material;

(b) a flange having a top surface and a bottom surface, wherein said nipple open end is coupled to said flange top surface;

(c) a locator case coupled to said flange bottom surface, wherein said locator case houses a receiver locator circuit including:

(i) a receiver configured to receive a locator signal and generate at least one enabling signal as a function of said locator signal;

(ii) a music module operatively coupled to said receiver and configured to generate preselected audible tones as a function of said at least one enabling signal;

(iii) a light emitting diode (LED) operatively coupled to said receiver and configured to illuminate responsive to another of said at least one enabling signal; and (iv) a battery;

wherein said the receiver locator circuit is configured to selectively operate in one of a plurality of operational modes and generate said audible tones and illuminate said LED either in concert or independently in response to said locator signal, wherein said operational modes include:

(A) a first mode wherein said audible tones are generated;

(B) a second mode wherein said LED illuminates; and (C) a third mode wherein said audible tones are generated and said LED is illuminated; and, (b) a remote transmitter case housing a transmitter circuit comprising:

(i) a user controllable selector having a plurality of mode settings, wherein each mode setting corresponds at least one of said operational modes;

(ii) a remote transmitter under operative control of said selector and configured to generate and transmit at a preselected frequency said locator signal, wherein said locator signal corresponds to said mode setting; and (iii) a battery.

* * * * *